(12) United States Patent
Wu et al.

(10) Patent No.: US 7,462,704 B2
(45) Date of Patent: Dec. 9, 2008

(54) TUMOR MARKER AND ITS USE

(75) Inventors: Jun Wu, Shanghai (CN); Ying Luo, Shanghai (CN)

(73) Assignee: Shanghai Genomics, Inc, Shanghai (CN)

( * ) Notice: Subject to any disclaimer, the term of this patent is extended or adjusted under 35 U.S.C. 154(b) by 8 days.

(21) Appl. No.: 10/547,397

(22) PCT Filed: Feb. 27, 2003

(86) PCT No.: PCT/CN03/00158

§ 371 (c)(1),
(2), (4) Date: Aug. 29, 2005

(87) PCT Pub. No.: WO2004/076480

PCT Pub. Date: Sep. 10, 2004

(65) Prior Publication Data

US 2006/0148013 A1      Jul. 6, 2006

(51) Int. Cl.
C07H 21/02    (2006.01)
C07H 21/04    (2006.01)
C12P 21/06    (2006.01)

(52) U.S. Cl. ............ 536/23.1; 536/23.5; 435/69.1
(58) Field of Classification Search ............. None
See application file for complete search history.

(56) References Cited

U.S. PATENT DOCUMENTS

2003/0105000 A1* 6/2003 Pero et al. ............ 514/12
2005/0074754 A1* 4/2005 Okubo et al. ............ 435/6

FOREIGN PATENT DOCUMENTS

WO      WO0183545      * 11/2001

OTHER PUBLICATIONS

Greenbaum et al. (Genome Biology, 2003, vol. 4, Issue 9, pp. 117.1-117.8).*
Brennan et al (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J., 1996, 15:43982-4401).*
Vallejo et al. (Biochimie, 2000 82:1129-1133).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No:850).*
Kaiser (Science, 2006, 313, 1370).*
Bowie et al (Science, 1990, 257:1306-1310).*
Burgess et al (J of Cell Bio. 111:2129-2138, 1990).*
Lazar et al. (Molecular and Cellular Biology 8:1247-1252 (1988)).*
Scott et al (Nature Genetics, 1999, 21:440-443).*
GenBank: NP631904, GI: 21040248, Dec. 23, 2002, Conejo-Garcia, J.-R., et al.
Bauer, et al. Activation of NK cells and T cells by NKG2D, a receptor for stress-inducible MICA. Science. 1999; 285(5428): 727-9.
Cerwenka, et al., Ectopic expression of retinoic acid early inducible-1 gene (RAE-1) permits natural killer cell-mediated rejection of a MHC class I-bearing tumor in vivo. Proc Natl Acad Sci USA. 2001; 98(20): 11521-6.
Cerwenka, et al., Retinoic acid early inducible genes define a ligand family for the activating NKG2D receptor in mice. Immunity. 2000; 12(6): 721-7.
Diefenbach, et al. Rael and H60 ligands of the NKG2D receptor stimulate tumour immunity. Nature. 2001; 413(6852): 165-71.
Wu, et al. An activating immunoreceptor complex formed by NKG2D and DAP10. Science. 1999; 285(5428): 730-2.
Yi Min, et al. Diagnostic value of the three tumour marker on gastric cancer. Journal of Wenzhou Medical College. 2001; 31(2). (In Chinese with English translation and certificate).
Zhang Zhenyu, et al. Diagnostic value of serum CEA, CA50, CA 19-9 and CA 125 on gastric cancer. Mod Diagn Treat. 2001; 12(3): 162. (In Chinese with English translation and certificate).

* cited by examiner

Primary Examiner—Karen A Canella
Assistant Examiner—Peter J Reddig
(74) Attorney, Agent, or Firm—Wilson Sonsini Goodrich & Rosati

(57) ABSTRACT

The invention provides a new kind of tumor marker RL9/RL10 protein, the polynucleotide encoding the polypeptide, and the method of producing RL9/RL10 protein by recombinant technology. The invention also discloses the use of RL9/RL10 protein and the polynucleotides encoding RL9/RL10 protein, e.g., in diagnosing and treating tumor, as well as the pharmaceutical composition containing RL9/RL10 protein or the antibody against it.

5 Claims, 4 Drawing Sheets

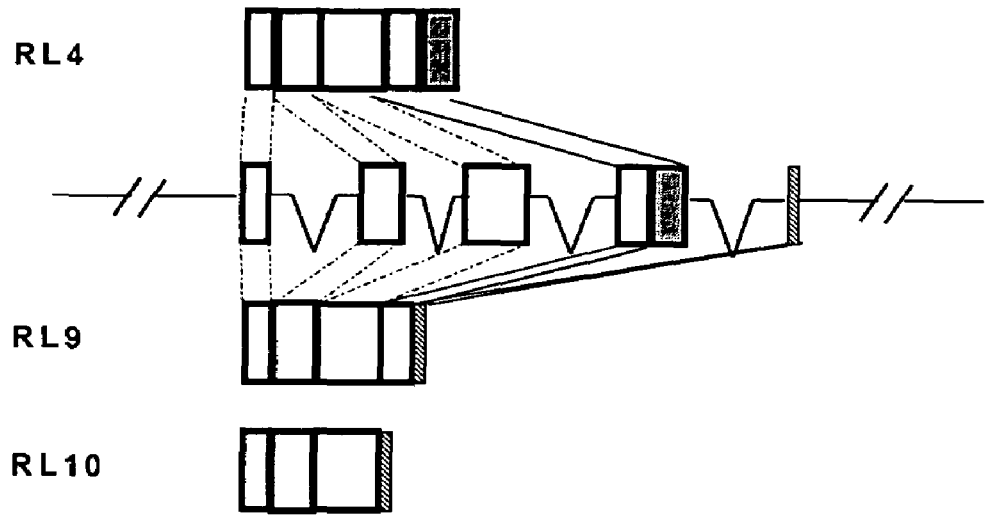

Fig. 2B

| | | |
|---|---|---|
| RL4  | 1   | MRRISLTSSP VHLLLFLLLL LIALEIMVGG HSLCFNFTIK SLSRPGQPWC |
| RL9  | 1   | MRRISLTSSP VHLLLFLLLL LIALEIMVGG HSLCFNFTIK SLSRPGQPWC |
| RL10 | 1   | MRRISLTSSP VRLLLFLLLL LIALEIMVGG HSLCFNFTIK SLSRPGQPWC |
| RL4  | 51  | EAQVFLNKNL FLQYNSDNNM VKPLGLLGKK VNATSTWGEL TQTLGEVGRD |
| RL9  | 51  | EAQVFLNKNL FLQYNSDNNM VKPLGLLGKK VNATSTWGEL TQTLGEVGRD |
| RL10 | 51  | EAQVFLNKNL FLQYNSDNNM VKPLGLLGKK VNATSTWGEL TQTLGEVGRD |
| RL4  | 101 | LRMLLCDIKP QIKTSDPSTL QVEMFCQREA ERCTGASWQF TINGEKSLLF |
| RL9  | 101 | LRMLLCDIKP QIKTSDPSTL QVEMFCQREA ERCTGASWQF TINGEKSLLF |
| RL10 | 101 | LRMLLCDIKP QIKTSDPSTL QVEMFCQREA ERCTGASWQF ATNGEKSLLF |
| RL4  | 151 | DAMNMTWTVI NHEASKIKET WKKDRGLEKY FRKLSKGDCD HWLREFLGHW |
| RL9  | 151 | DAMNMTWTVI NHEASKIKET WKKDRGLEKY FRKLSKGDCD HWLREFLGHW |
| RL10 | 151 | DAMNMTWTVI NHEASKIKET WKKDRGLEKY FRKLSKGDCD HWLREFLGHW |
| RL4  | 201 | EAMPEPTVSP VNASDIHWSS SSLPDRWIIL GAFILLLLMG IVLICVWWQN |
| RL9  | 201 | EAMPEPTVSP VNASDIHWSS SSLPDRWIIL GAFILLLLMG IVLICVWWQN |
| RL10 | 201 | EAMPEPT--- ---------- ---------- ---------- ---------- |
| RL4  | 251 | GEWQAGLWPL RTS |
| RL9  | 251 | ---------- --- GRRST |
| RL10 | 208 | ---------- --- GRRST |

Fig. 3

| | | |
|---|---|---|
| RL4  | ATGCGAAGAATATCCCTGACTTCTAGCCCTGTGCACCTTCTTTTGTTTCTGCTGTTGCTA | 60 |
| RL9  | ATGCGAAGAATATCCCTGACTTCTAGCCCTGTGCACCTTCTTTTGTTTCTGCTGTTGCTA | 60 |
| RL10 | ATGCGAAGAATATCCCTGACTTCTAGCCCTGTGCGCCTTCTTTTGTTTCTGCTGTTGCTA | 60 |
| | ********************************** ************************ | |

| | | |
|---|---|---|
| RL4  | CTAATAGCCTTGGAGATCATGGTTGGTGGTCACTCTCTTTGCTTCAACTTCACTATAAAA | 120 |
| RL9  | CTAATAGCCTTGGAGATCATGGTTGGTGGTCACTCTCTTTGCTTCAACTTCACTATAAAA | 120 |
| RL10 | CTAATAGCCTTGGAGATCATGGTTGGTGGTCACTCTCTTTGCTTCAACTTCACTATAAAA | 120 |
| | ************************************************************ | |

| | | |
|---|---|---|
| RL4  | TCATTGTCCAGACCTGGACAGCCCTGGTGTGAAGCGCAGGTCTTCTTGAATAAAAATCTT | 180 |
| RL9  | TCATTGTCCAGACCTGGACAGCCCTGGTGTGAAGCGCAGGTCTTCTTGAATAAAAATCTT | 180 |
| RL10 | TCATTGTCCAGACCTGGACAGCCCTGGTGTGAAGCGCAGGTCTTCTTGAATAAAAATCTT | 180 |
| | ************************************************************ | |

| | | |
|---|---|---|
| RL4  | TTCCTTCAGTACAACAGTGACAACAACATGGTCAAACCTCTGGGCCTCCTGGGGAAGAAG | 240 |
| RL9  | TTCCTTCAGTACAACAGTGACAACAACATGGTCAAACCTCTGGGCCTCCTGGGGAAGAAG | 240 |
| RL10 | TTCCTTCAGTACAACAGTGACAACAACATGGTCAAACCTCTGGGCCTCCTGGGGAAGAAG | 240 |
| | ************************************************************ | |

| | | |
|---|---|---|
| RL4  | GTAAATGCCACCAGCACTTGGGGAGAATTGACCCAAACGCTGGGAGAAGTGGGGCGAGAC | 300 |
| RL9  | GTAAATGCCACCAGCACTTGGGGAGAATTGACCCAAACGCTGGGAGAAGTGGGGCGAGAC | 300 |
| RL10 | GTAAATGCCACCAGCACTTGGGGAGAATTGACCCAAACGCTGGGAGAAGTGGGGCGAGAC | 300 |
| | ************************************************************ | |

| | | |
|---|---|---|
| RL4  | CTCAGGATGCTCCTTTGTGACATCAAACCCCAGATAAAGACCAGTGATCCTTCCACTCTG | 360 |
| RL9  | CTCAGGATGCTCCTTTGTGACATCAAACCCCAGATAAAGACCAGTGATCCTTCCACTCTG | 360 |
| RL10 | CTCAGGATGCTCCTTTGTGACATCAAACCCCAGATAAAGACCAGTGATCCTTCCACTCTG | 360 |
| | ************************************************************ | |

| | | |
|---|---|---|
| RL4  | CAAGTCGAGATGTTTTGTCAACGTGAAGCAGAACGGTGCACTGGTGCATCCTGGCAGTTC | 420 |
| RL9  | CAAGTCGAGATGTTTTGTCAACGTGAAGCAGAACGGTGCACTGGTGCATCCTGGCAGTTC | 420 |
| RL10 | CAAGTCGAGATGTTTTGTCAACGTGAAGCAGAACGGTGCACTGGTGCATCCTGGCAGTTC | 420 |
| | ************************************************************ | |

| | | |
|---|---|---|
| RL4  | ACCATCAATGGAGAGAAATCCCTCCTCTTTGACGCAATGAACATGACCTGGACAGTAATT | 480 |
| RL9  | ACCATCAATGGAGAGAAATCCCTCCTCTTTGACGCAATGAACATGACCTGGACAGTAATT | 480 |
| RL10 | GCCACCAATGGAGAGAAATCCCTCCTCTTTGACGCAATGAACATGACCTGGACAGTAATT | 480 |
| | ***  ******************************************************* | |

| | | |
|---|---|---|
| RL4  | AATCATGAAGCCAGTAAGATCAAGGAGACATGGAAGAAAGACAGAGGGCTGGAAAAGTAT | 540 |
| RL9  | AATCATGAAGCCAGTAAGATCAAGGAGACATGGAAGAAAGACAGAGGGCTGGAAAAGTAT | 540 |
| RL10 | AATCATGAAGCCAGTAAGATCAAGGAGACATGGAAGAAAGACAGAGGGCTGGAAAAGTAT | 540 |
| | ************************************************************ | |

| | | |
|---|---|---|
| RL4  | TTCAGGAAGCTCTCAAAGGGAGACTGCGATCACTGGCTCAGGGAATTCTTAGGGCACTGG | 600 |
| RL9  | TTCAGGAAGCTCTCAAAGGGAGACTGCGATCACTGGCTCAGGGAATTCTTAGGGCACTGG | 600 |
| RL10 | TTCAGGAAGCTCTCAAAGGGAGACTGCGATCACTGGCTCAGGGAATTCTTAGGGCACTGG | 600 |
| | ************************************************************ | |

| | | |
|---|---|---|
| RL4  | GAGGCAATGCCAGAACCGACAGTGTCACCAGTAAATGCTTCAGATATCCACTGGTCTTCT | 660 |
| RL9  | GAGGCAATGCCAGAACCGACAGTGTCACCAGTAAATGCTTCAGATATCCACTGGTCTTCT | 660 |
| RL10 | GAGGCAATGCCAGAACCGACA--------------------------------------- | 639 |
| | ********************* | |

| | | |
|---|---|---|
| RL4  | TCTAGTCTACCAGATAGATGGATCATCCTGGGGGCATTCATCCTGTTACTTTTAATGGGA | 720 |
| RL9  | TCTAGTCTACCAGATAGATGGATCATCCTGGGGGCATTCATCCTGTTACTTTTAATGGGA | 720 |
| RL10 | ------------------------------------------------------------ | |

| | | |
|---|---|---|
| RL4  | ATTGTTCTCATCTGTGTCTGGTGGCAAAATGGTGAGTGG-CAGGCTGGTCTCTGGCCCTT | 779 |
| RL9  | ATTGTTCTCATCTGTGTCTGGTGGCAAAAT----------------------------- | 768 |
| RL10 | ------------------------------------------------------------ | |

| | | |
|---|---|---|
| RL4  | GAGGACGTCTTAG | 792 |
| RL9  | -------------GGCAGAAGATCCACCTAG | |
| RL10 | -------------GGCAGAAGATCCACCTAG | |

Fig. 4

SEQUENCE LISTING

<160> NUMBER OF SEQ ID NOS: 12

<210> SEQ ID NO 1
<211> LENGTH: 1267
<212> TYPE: DNA
<213> ORGANISM: Homo sapiens
<220> FEATURE:
<221> NAME/KEY: CDS
<222> LOCATION: (1)..(768)
<223> OTHER INFORMATION:

<400> SEQUENCE: 1

```
atg cga aga ata tcc ctg act tct agc cct gtg cac ctt ctt ttg ttt        48
Met Arg Arg Ile Ser Leu Thr Ser Ser Pro Val His Leu Leu Leu Phe
1               5                   10                  15 ctg ctg ttg cta cta ata gcc ttg gag atc atg gtt ggt ggt cac tct        96
Leu Leu Leu Leu Leu Ile Ala Leu Glu Ile Met Val Gly Gly His Ser
            20                  25                  30 ctt tgc ttc aac ttc act ata aaa tca ttg tcc aga cct gga cag ccc       144
Leu Cys Phe Asn Phe Thr Ile Lys Ser Leu Ser Arg Pro Gly Gln Pro
        35                  40                  45 tgg tgt gaa gcg cag gtc ttc ttg aat aaa aat ctt ttc ctt cag tac       192
Trp Cys Glu Ala Gln Val Phe Leu Asn Lys Asn Leu Phe Leu Gln Tyr
    50                  55                  60 aac agt gac aac aac atg gtc aaa cct ctg ggc ctc ctg ggg aag aag       240
Asn Ser Asp Asn Asn Met Val Lys Pro Leu Gly Leu Leu Gly Lys Lys
65                  70                  75                  80 gta aat gcc acc agc act tgg gga gaa ttg acc caa acg ctg gga gaa       288
Val Asn Ala Thr Ser Thr Trp Gly Glu Leu Thr Gln Thr Leu Gly Glu
                85                  90                  95 gtg ggg cga gac ctc agg atg ctc ctt tgt gac atc aaa ccc cag ata       336
Val Gly Arg Asp Leu Arg Met Leu Leu Cys Asp Ile Lys Pro Gln Ile
            100                 105                 110 aag acc agt gat cct tcc act ctg caa gtc gag atg ttt tgt caa cgt       384
Lys Thr Ser Asp Pro Ser Thr Leu Gln Val Glu Met Phe Cys Gln Arg
        115                 120                 125 gaa gca gaa cgg tgc act ggt gca tcc tgg cag ttc acc atc aat gga       432
Glu Ala Glu Arg Cys Thr Gly Ala Ser Trp Gln Phe Thr Ile Asn Gly
    130                 135                 140 gag aaa tcc ctc ctc ttt gac gca atg aac atg acc tgg aca gta att       480
Glu Lys Ser Leu Leu Phe Asp Ala Met Asn Met Thr Trp Thr Val Ile
145                 150                 155                 160 aat cat gaa gcc agt aag atc aag gag aca tgg aag aaa gac aga ggg       528
Asn His Glu Ala Ser Lys Ile Lys Glu Thr Trp Lys Lys Asp Arg Gly
                165                 170                 175 ctg gaa aag tat ttc agg aag ctc tca aag gga gac tgc gat cac tgg       576
Leu Glu Lys Tyr Phe Arg Lys Leu Ser Lys Gly Asp Cys Asp His Trp
            180                 185                 190 ctc agg gaa ttc tta ggg cac tgg gag gca atg cca gaa ccg aca gtg       624
Leu Arg Glu Phe Leu Gly His Trp Glu Ala Met Pro Glu Pro Thr Val
        195                 200                 205 tca cca gta aat gct tca gat atc cac tgg tct tct tct agt cta cca       672
Ser Pro Val Asn Ala Ser Asp Ile His Trp Ser Ser Ser Ser Leu Pro
    210                 215                 220 gat aga tgg atc atc ctg ggg gca ttc atc ctg tta ctt tta atg gga       720
Asp Arg Trp Ile Ile Leu Gly Ala Phe Ile Leu Leu Leu Leu Met Gly
225                 230                 235                 240 att gtt ctc atc tgt gtc tgg tgg caa aat ggc aga aga tcc acc tag       768
Ile Val Leu Ile Cys Val Trp Trp Gln Asn Gly Arg Arg Ser Thr
                245                 250                 255
```

```
aggtgatacc acggcggcgc agagttgttc acctgtggtc ctcgatcgct gacagccttg    828
gctcccactg ctgtgtgttc cctgagtcaa gtggaggcgg agcctgcaat gagcggagat    888
cgcgcctctg cattccagtc ttggcaacag agcaagactc cgtctcaaaa aaaaaaaatt    948
ttttttcagt acatatttt  taaaagatag ggctggccac agcagctcac atctataatc   1008
ccaacacttt gggaggccta ggcaggagga tcacttgagc caggaatctg aagctgcagt   1068
gagcctttgc tcgtgagatt gtggacctat gatcctacca ccagcccacc tggttctaac   1128
accccctcct ctatgtgtga gagggagaga agaaaagtga ggaatcgaat tcccgcggcc   1188
gccatggcgc cgggagcatg cgacgtcggc ccaattcgac atatagagag tcgtatacat   1248
tcctgcctaa agtgccccc                                                1267
```

<210> SEQ ID NO 2
<211> LENGTH: 255
<212> TYPE: PRT
<213> ORGANISM: Homo sapiens

<400> SEQUENCE: 2

```
Met Arg Arg Ile Ser Leu Thr Ser Ser Pro Val His Leu Leu Leu Phe
  1               5                  10                  15

Leu Leu Leu Leu Leu Ile Ala Leu Glu Ile Met Val Gly Gly His Ser
             20                  25                  30

Leu Cys Phe Asn Phe Thr Ile Lys Ser Leu Ser Arg Pro Gly Gln Pro
         35                  40                  45

Trp Cys Glu Ala Gln Val Phe Leu Asn Lys Asn Leu Phe Leu Gln Tyr
     50                  55                  60

Asn Ser Asp Asn Met Val Lys Pro Leu Gly Leu Leu Gly Lys Lys
 65                  70                  75                  80

Val Asn Ala Thr Ser Thr Trp Gly Glu Leu Thr Gln Thr Leu Gly Glu
                 85                  90                  95

Val Gly Arg Asp Leu Arg Met Leu Leu Cys Asp Ile Lys Pro Gln Ile
            100                 105                 110

Lys Thr Ser Asp Pro Ser Thr Leu Gln Val Glu Met Phe Cys Gln Arg
        115                 120                 125

Glu Ala Glu Arg Cys Thr Gly Ala Ser Trp Gln Phe Thr Ile Asn Gly
    130                 135                 140

Glu Lys Ser Leu Leu Phe Asp Ala Met Asn Met Thr Trp Thr Val Ile
145                 150                 155                 160

Asn His Glu Ala Ser Lys Ile Lys Glu Thr Trp Lys Lys Asp Arg Gly
                165                 170                 175

Leu Glu Lys Tyr Phe Arg Lys Leu Ser Lys Gly Asp Cys Asp His Trp
            180                 185                 190

Leu Arg Glu Phe Leu Gly His Trp Glu Ala Met Pro Glu Pro Thr Val
        195                 200                 205

Ser Pro Val Asn Ala Ser Asp Ile His Trp Ser Ser Ser Leu Pro
    210                 215                 220

Asp Arg Trp Ile Ile Leu Gly Ala Phe Ile Leu Leu Leu Met Gly
225                 230                 235                 240

Ile Val Leu Ile Cys Val Trp Trp Gln Asn Gly Arg Arg Ser Thr
                245                 250                 255
```

<210> SEQ ID NO 3
<211> LENGTH: 1043
<212> TYPE: DNA

<213> ORGANISM: Homo sapiens
<220> FEATURE:
<221> NAME/KEY: CDS
<222> LOCATION: (1)..(639)
<223> OTHER INFORMATION:

<400> SEQUENCE: 3

```
atg cga aga ata tcc ctg act tct agc cct gtg cgc ctt ctt ttg ttt      48
Met Arg Arg Ile Ser Leu Thr Ser Ser Pro Val Arg Leu Leu Leu Phe
1               5                   10                  15 ctg ctg ttg cta cta ata gcc ttg gag atc atg gtt ggt ggt cac tct      96
Leu Leu Leu Leu Leu Ile Ala Leu Glu Ile Met Val Gly Gly His Ser
                20                  25                  30 ctt tgc ttc aac ttc act ata aaa tca ttg tcc aga cct gga cag ccc     144
Leu Cys Phe Asn Phe Thr Ile Lys Ser Leu Ser Arg Pro Gly Gln Pro
            35                  40                  45 tgg tgt gaa gcg cag gtc ttc ttg aat aaa aat ctt ttc ctt cag tac     192
Trp Cys Glu Ala Gln Val Phe Leu Asn Lys Asn Leu Phe Leu Gln Tyr
        50                  55                  60 aac agt gac aac aac atg gtc aaa cct ctg ggc ctc ctg ggg aag aag     240
Asn Ser Asp Asn Asn Met Val Lys Pro Leu Gly Leu Leu Gly Lys Lys
65                  70                  75                  80 gta aat gcc acc agc act tgg gga gaa ttg acc caa acg ctg gga gaa     288
Val Asn Ala Thr Ser Thr Trp Gly Glu Leu Thr Gln Thr Leu Gly Glu
                85                  90                  95 gtg ggg cga gac ctc agg atg ctc ctt tgt gac atc aaa ccc cag ata     336
Val Gly Arg Asp Leu Arg Met Leu Leu Cys Asp Ile Lys Pro Gln Ile
                100                 105                 110 aag acc agt gat cct tcc act ctg caa gtc gag atg ttt tgt caa cgt     384
Lys Thr Ser Asp Pro Ser Thr Leu Gln Val Glu Met Phe Cys Gln Arg
            115                 120                 125 gaa gca gaa cgg tgc act ggt gca tcc tgg cag ttc gcc acc aat gga     432
Glu Ala Glu Arg Cys Thr Gly Ala Ser Trp Gln Phe Ala Thr Asn Gly
130                 135                 140 gag aaa tcc ctc ctc ttt gac gca atg aac atg acc tgg aca gta att     480
Glu Lys Ser Leu Leu Phe Asp Ala Met Asn Met Thr Trp Thr Val Ile
145                 150                 155                 160 aat cat gaa gcc agt aag atc aag gag aca tgg aag aaa gac aga ggg     528
Asn His Glu Ala Ser Lys Ile Lys Glu Thr Trp Lys Lys Asp Arg Gly
                165                 170                 175 ctg gaa aag tat ttc agg aag ctc tca aag gga gac tgc gat cac tgg     576
Leu Glu Lys Tyr Phe Arg Lys Leu Ser Lys Gly Asp Cys Asp His Trp
            180                 185                 190 ctc agg gaa ttc tta ggg cac tgg gag gca atg cca gaa ccg aca ggc     624
Leu Arg Glu Phe Leu Gly His Trp Glu Ala Met Pro Glu Pro Thr Gly
        195                 200                 205 aga aga tcc acc tag aggtgatacc acggcggcgc agagttgttc acctgtggtc     679
Arg Arg Ser Thr
        210 ctcgatcgct gacagccttg gctcccactg ctgcgtgttc cctgagtcaa gtggaggcgg     739 agcctgcaat gagcggagat cgcgcctctg cattccagtc ttggcaacag agcaagactc     799 cgtctcaaaa aaaaaaaaat ttttttcag tacatatttt ttaaaagata gggctgggca     859 cagcagctca catctataat cccaacactt tgggaggcct aggcaggagg atcgcttgag     919 cccaggaatc tgaagctgca gtgagccttt gctcgtgaga ttgtggacct atgatcctac     979 caccagccca cctggttcta acaccccctc ctctatgtgt gagagggaga gaagaaaagt     1039 gagg                                                                 1043
```

<210> SEQ ID NO 4
<211> LENGTH: 212
<212> TYPE: PRT
<213> ORGANISM: Homo sapiens

<400> SEQUENCE: 4

```
Met Arg Arg Ile Ser Leu Thr Ser Ser Pro Val Arg Leu Leu Leu Phe
1               5                   10                  15

Leu Leu Leu Leu Leu Ile Ala Leu Glu Ile Met Val Gly Gly His Ser
            20                  25                  30

Leu Cys Phe Asn Phe Thr Ile Lys Ser Leu Ser Arg Pro Gly Gln Pro
        35                  40                  45

Trp Cys Glu Ala Gln Val Phe Leu Asn Lys Asn Leu Phe Leu Gln Tyr
    50                  55                  60

Asn Ser Asp Asn Asn Met Val Lys Pro Leu Gly Leu Leu Gly Lys Lys
65                  70                  75                  80

Val Asn Ala Thr Ser Thr Trp Gly Glu Leu Thr Gln Thr Leu Gly Glu
                85                  90                  95

Val Gly Arg Asp Leu Arg Met Leu Leu Cys Asp Ile Lys Pro Gln Ile
            100                 105                 110

Lys Thr Ser Asp Pro Ser Thr Leu Gln Val Glu Met Phe Cys Gln Arg
        115                 120                 125

Glu Ala Glu Arg Cys Thr Gly Ala Ser Trp Gln Phe Ala Thr Asn Gly
    130                 135                 140

Glu Lys Ser Leu Leu Phe Asp Ala Met Asn Met Thr Trp Thr Val Ile
145                 150                 155                 160

Asn His Glu Ala Ser Lys Ile Lys Glu Thr Trp Lys Lys Asp Arg Gly
                165                 170                 175

Leu Glu Lys Tyr Phe Arg Lys Leu Ser Lys Gly Asp Cys Asp His Trp
            180                 185                 190

Leu Arg Glu Phe Leu Gly His Trp Glu Ala Met Pro Glu Pro Thr Gly
        195                 200                 205

Arg Arg Ser Thr
    210
```

<210> SEQ ID NO 5
<211> LENGTH: 26
<212> TYPE: DNA
<213> ORGANISM: Artificial sequence
<220> FEATURE:
<221> NAME/KEY: misc_feature
<222> LOCATION: (1)..(26)
<223> OTHER INFORMATION: primer

<400> SEQUENCE: 5
atgcgaagaa tatccctgac ttctag                                              26

<210> SEQ ID NO 6
<211> LENGTH: 32
<212> TYPE: DNA
<213> ORGANISM: Artificial sequence
<220> FEATURE:
<221> NAME/KEY: misc_feature
<222> LOCATION: (1)..(32)
<223> OTHER INFORMATION: primer

<400> SEQUENCE: 6
cctcactttt cttctctccc tctcacacat ag                                       32

<210> SEQ ID NO 7

```
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 7
gacctggaca gtaattaatc                                              20

<210> SEQ ID NO 8
<211> LENGTH: 18
<212> TYPE: DNA
<213> ORGANISM: Artificial sequence
<220> FEATURE:
<221> NAME/KEY: misc_feature
<222> LOCATION: (1)..(18)
<223> OTHER INFORMATION: primer

<400> SEQUENCE: 8
ttgactcagg gaacacac                                                18

<210> SEQ ID NO 9
<211> LENGTH: 792
<212> TYPE: DNA
<213> ORGANISM: Homo sapiens

<400> SEQUENCE: 9
atgcgaagaa tatccctgac ttctagccct gtgcaccttc ttttgtttct gctgttgcta    60
ctaatagcct tggagatcat ggttggtggt cactctcttt gcttcaactt cactataaaa   120
tcattgtcca gacctggaca gccctggtgt gaagcgcagg tcttcttgaa taaaaatctt   180
ttccttcagt acaacagtga caacaacatg gtcaaacctc tgggcctcct ggggaagaag   240
gtaaatgcca ccagcacttg gggagaattg acccaaacgc tggagaagt ggggcgagac    300 ctcaggatgc tcctttgtga catcaaaccc cagataaaga ccagtgatcc ttccactctg   360
caagtcgaga tgttttgtca acgtgaagca gaacggtgca ctggtgcatc ctggcagttc   420
accatcaatg gagagaaatc cctcctcttt gacgcaatga acatgacctg gacagtaatt   480
aatcatgaag ccagtaagat caaggagaca tggaagaaag acagagggct ggaaaagtat   540
ttcaggaagc tctcaaaggg agactgcgat cactggctca gggaattctt agggcactgg   600
gaggcaatgc cagaaccgac agtgtcacca gtaaatgctt cagatatcca ctggtcttct   660
tctagtctac cagatagatg gatcatcctg ggggcattca tcctgttact tttaatggga   720
attgttctca tctgtgtctg gtggcaaaat ggtgagtggc aggctggtct ctggcccttg   780
aggacgtctt ag                                                       792

<210> SEQ ID NO 10
<211> LENGTH: 263
<212> TYPE: PRT
<213> ORGANISM: Homo sapiens

<400> SEQUENCE: 10

Met Arg Arg Ile Ser Leu Thr Ser Ser Pro Val His Leu Leu Leu Phe
1               5                   10                  15

Leu Leu Leu Leu Leu Ile Ala Leu Glu Ile Met Val Gly Gly His Ser
            20                  25                  30

Leu Cys Phe Asn Phe Thr Ile Lys Ser Leu Ser Arg Pro Gly Gln Pro
        35                  40                  45
```

```
-continued

Trp Cys Glu Ala Gln Val Phe Leu Asn Lys Asn Leu Phe Leu Gln Tyr
    50                  55                  60

Asn Ser Asp Asn Asn Met Val Lys Pro Leu Gly Leu Leu Gly Lys Lys
65                  70                  75                  80

Val Asn Ala Thr Ser Thr Trp Gly Glu Leu Thr Gln Thr Leu Gly Glu
                85                  90                  95

Val Gly Arg Asp Leu Arg Met Leu Leu Cys Asp Ile Lys Pro Gln Ile
            100                 105                 110

Lys Thr Ser Asp Pro Ser Thr Leu Gln Val Glu Met Phe Cys Gln Arg
            115                 120                 125

Glu Ala Glu Arg Cys Thr Gly Ala Ser Trp Gln Phe Thr Ile Asn Gly
            130                 135                 140

Glu Lys Ser Leu Leu Phe Asp Ala Met Asn Met Thr Trp Thr Val Ile
145                 150                 155                 160

Asn His Glu Ala Ser Lys Ile Lys Glu Thr Trp Lys Lys Asp Arg Gly
                165                 170                 175

Leu Glu Lys Tyr Phe Arg Lys Leu Ser Lys Gly Asp Cys Asp His Trp
            180                 185                 190

Leu Arg Glu Phe Leu Gly His Trp Glu Ala Met Pro Glu Pro Thr Val
            195                 200                 205

Ser Pro Val Asn Ala Ser Asp Ile His Trp Ser Ser Ser Ser Leu Pro
210                 215                 220

Asp Arg Trp Ile Ile Leu Gly Ala Phe Ile Leu Leu Leu Met Gly
225                 230                 235                 240

Ile Val Leu Ile Cys Val Trp Trp Gln Asn Gly Glu Trp Gln Ala Gly
                245                 250                 255

Leu Trp Pro Leu Arg Thr Ser
            260

<210> SEQ ID NO 11
<211> LENGTH: 34
<212> TYPE: DNA
<213> ORGANISM: Artificial sequence
<220> FEATURE:
<221> NAME/KEY: misc_feature
<222> LOCATION: (1)..(34)
<223> OTHER INFORMATION: primer

<400> SEQUENCE: 11
ccgggatcct tggagatcat ggttggtggt cact                              34

<210> SEQ ID NO 12
<211> LENGTH: 35
<212> TYPE: DNA
<213> ORGANISM: Artificial sequence
<220> FEATURE:
<221> NAME/KEY: misc_feature
<222> LOCATION: (1)..(35)
<223> OTHER INFORMATION: primer

<400> SEQUENCE: 12
ggccaagctt ccatctatct ggtagactag aagaa                             35
```

TUMOR MARKER AND ITS USE

CROSS-REFERENCE TO RELATED APPLICATION

This Application is a Section 371 National Stage Application of International Application No. PCT/CN2003/000158, filed 27 Feb. 2003 and published as WO 2004/076480 A1 on 10 Sep. 2004 and claims the priority thereof, the subject matter of which is hereby incorporated by reference in its entirety.

FIELD OF INVENTION

This invention relates to the field of biotechnology and medicine. In particular, it relates to novel tumor markers of RL9 and RL10 proteins, the polynucleotides encoding RL9 and RL10 proteins, and the method of producing RL9 and RL10 proteins by recombinant technology. The invention also discloses the use of RL9 and RL10 proteins and the polynucleotides encoding RL9 and RL10 protein, e.g., in diagnosing and treating tumor, as well as the pharmaceutical composition containing RL9 and RL10 proteins or the antibodies against them.

TECHNICAL BACKGROUND

Since the 1950's, cancer diagnosis and treatment have made significant progress, particularly in the areas of identification of tumor-specific oncogenes and tumor suppressor genes.

Forty years ago, Lewis Thomas and Macfarlane Burnet proposed an immune surveillance mechanism against malignant cells. Recent studies on natural killer cells and T cells have not only provided new evidences supporting such hypothesis, but also uncovered a potential molecular mechanism underlining the immune surveillance process.

Natural killer cells (NK cells) are critical players involved in the first line of defense against pathogens and other detrimental signals. NK cells are capable of recognizing target cells and subsequently eliminating these cells through secretion of cytotoxic mediators. Since NK cells' function does not depend upon antigen/mitogen stimulation, nor does it require mediation through antibody or complement, these cells therefore should possess a recognition system to distinguish between normal and unhealthy targets. The current view is the NK cell function is regulated through a balance between its surface activating and inhibitory receptors. Major histocompatibility complex (MHC) class-1 molecules on the surface of all cells are recognized by NK cell receptors, including murine Ly49 (recognizing H-2K and H-2D) and human killer inhibitory receptors (KIR) (recognizing HLA-A, -B, -C), resulting in inhibiting NK cell's function. In viral-infected or tumor cells, these MHC class-1 molecules are frequently down regulated. A reduction of the engagement of the inhibitory receptors on NK cells causes the activation of NK cells, thereby killing these abnormal cells.

In addition to NK cells, T cells are also involved in preventing skin cancer formation induced by certain carcinogens. In human and mice, γδ-T cells in skin and gut epithelium are known to participate in local immunity. It has been shown that these T cells are involved in immune surveillance against transformation of gut epithelial cells. Moreover, recent studies have also demonstrated that these T cells are important players in eliminating transformed cells induced by exogenous carcinogen. The induction of two MHC class-I related molecules, MIC-A and MIC-B, on abnormal cells has been shown to be involved in the immune surveillance processes.

Bauer et al (Bauer S, et al., Science 1999 Jul. 30,; 285 (5428): 727-9) have identified NKG2D as a receptor for MIC-A and MIC-B through representational differential analysis (RDA), which is a orphan C-type lectin-like NK cell receptor with unknown expression and function.

Several NK cell receptors, which are specific to MHC-1 or the MHC-1-related molecules, have been found. Unlike other NK cell receptors, NKG2D is an activating receptor present on all NK cells, γδ-T cells, and some CD8+ T cells. It forms a receptor complex with a transmembrane signaling adaptor, DAP10, in which its cytoplasmic domain contains a YxxM sequence motif capable of activating P13 kinase-mediated signaling pathways (Wu J, et al., Science 1999 Jul. 30; 285 (5428): 730-2).

There is no MICA or MICB homologue in mice. However, it was subsequently found in mice that a family of glycoproteins called RAE-1 also served as ligands for murine NKG2D (Cerwenka A, et al., Immunity 2000 Jun. 12; (6): 721-7). Recent studies have revealed that there are at least five RAE-1 molecules (RAE-1-α, -β, -γ, -δ, -ε) and one RAE-1-related molecule H60. These molecules are absent or low expressed in normal tissues but are highly expressed in certain malignant tissues or upon treatment with retinoic acid. Their expression can also be found in tumors induced by carcinogen TPA. Recent studies by Diefenbach et al. (Nature 2001 Sep. 13; 413(6852): 165-71) and Cerwenka et al. (Proc Natl Acad Sci USA 2001 Sep. 25; 98 (20): 11521-6) have demonstrated that transfection of RAE-1 in MHC class-I expressing tumor cells results in rejection of these tumors by NK cells in mice. Similar to NK cells, murine γδ-T cells can also kill inoculated squamous carcinoma cell line in vivo via NKG2D, and under certain experimental conditions, RAE-1 can induce γδ-T cell memory response against transplanted tumors.

The subsequent studies have uncovered RAE-1 homologues in human, including ULBP-1, ULBP-2, and ULBP-3. These molecules were initially identified as interacting partners with human cytomegaloviral glycoprotein UL16. Although ULBP molecules are related to MHC class-1, they are not close to MICB, which is also capable to bind UL16. ULBP is also the ligand for NKG2D and is capable to stimulate NK cell to express cytokine and chemokine. The expression of ULBP in target cells against NK cells prevent them from attacking by NK cells. In the cytomegalovirus infection, the ULBP or MIC antigen may be veiled by UL16 protein so as to avoid the attacks from the immune system.

Taken together, numerous studies in human and mice indicate NKG2D plays a vital role in immune responses mediated by NK cells, γδ-TCR+T cells, CD8+α,β-TCR+ T cells against virus and tumors. However, the activation mechanism of NKG2D is poorly elucidated so far.

Since the 1990's, research in tumor immunology has made some breakthroughs. Immune treatment of cancer comes to a new era. Many immune treatments have been in clinical level, mainly by activating the immune cells of patients in vivo or in vitro to recognize malignant cells. The further proliferation of such immune cells eliminates or inhibits the growth of malignant cells.

In the research of tumor immunology, human tumor rejection antigen was discovered for the first time in 1991. From then on, numerous studies indicate that most of the tumor cells have different molecules from normal cells, which could be recognized and attacked by immune system. Such molecules are called tumor rejection antigen. Human immune cells capable of tumor killing can be induced in vivo and in vitro by tumor rejection antigen. Therefore, tumor rejection antigens are the most important component in tumor immune treatment.

So far, several tumor antigens have been discovered in melanoma and other tumor tissues including prostate tumor, thymus tumor, ovarian tumor and gastrointestinal tumor. Tumor rejection antigens discovered by now are classified into four types. The first type is from somatic mutations of normal genes and the second is from the mutation of genes related to tumor progressing. These two types have patient specificity, which are not available for generalized treatment. The third type of antigen expresses in normal tissues but their expression levels are highly elevated in tumors. If their genes are not mutated, these antigens are universal in tumor patients. However, they have strict tissue specificity rather than tumor specificity so that they do not have significance in clinical treatment. The fourth type has strict tumor specificity and is related to tumor progression. Because they are widely expressed in humor tumor, these tumor antigens are suitable candidates to be tumor markers and targets of anti-tumor immune response. However, very few antigens discovered by now belong to the fourth type.

Therefore, there is a keen need in the art to develop new tumor rejection antigen of the fourth type, which can be used as a tumor tag for tumor diagnosis and treatment.

SUMMARY OF INVENTION

One purpose of the invention is to provide novel human tumor tags (i.e., tumor markers), which were named RL9 and RL10 proteins, and their fragments, analogs and derivatives.

Another purpose of the invention is to provide a polynucleotide encoding said polypeptides.

Still another purpose of the invention is to provide a method for preparing said polypeptides and the use of said polypeptides and their encoding sequences.

After comprehensive and intensive researches, the inventors have found and isolated two novel antigen genes, RL9 and RL10, which are useful as tumor tags. RL9 and RL10 genes are not expressed or low expressed in normal tissues, but are widely expressed in tumor tissues. The expression products of RL9 and RL10 are secretory proteins. RL9 and RL10 bind to NKG2D receptors with high efficiency. On the basis of said discovery, the inventors completed this invention.

In the 1st aspect, the invention provides the isolated RL9 or RL10 polypeptides, which comprise a polypeptide having the amino acid sequence of SEQ ID NOs: 2 or 4, and the conservative variants, active fragments, and active derivatives thereof. Preferably, the polypeptide consists of the amino acid sequence as shown in SEQ ID NOs: 2 or 4.

In the 2nd aspect, it provides an isolated polynucleotide comprising a nucleotide sequence sharing at least 70% identity to the following nucleotide sequences: (a) a polynucleotide encoding the RL9 or RL10 polypeptide; (b) the polynucleotide complementary to polynucleotide of (a). Preferably, said polynucleotide encodes a polypeptide comprising the amino acid sequence of SEQ ID NOs: 2 or 4. More preferably, said polynucleotide is selected from the group consisting of (a) the nucleotide sequence of 1-768 of SEQ ID NO: 1; (b) the nucleotide sequence of 1-1267 of SEQ ID NO: 1; (c) the nucleotide sequence of 1-639 of SEQ ID NO: 3; and (d) the nucleotide sequence of 1-1043 of SEQ ID NO: 3.

In the 3rd aspect, it provides a vector comprising the above polynucleotide, and a host cell transformed with the vector or polynucleotide.

In the 4th aspect, it provides a method for producing RL9 or RL10 protein, which comprises:
(a) culturing the above transformed host cell under the expression conditions;
(b) isolating RL9 or RL10 protein from the culture.

In the 5th aspect, it provides an antibody specifically binding RL9 and/or RL10 protein. Also provided are nucleic acid molecules comprising consecutive 20-1000 nucleotides of the above polynucleotide.

In the 6th aspect, it provides compounds that simulate, promote and antagonize RL9 and/or RL10 activity, or inhibit RL9 and/or RL10 expression and methods for screening and preparing these compounds. Preferably, the compounds are antisense sequences of RL9 and/or RL10 encoding sequence or fragments thereof.

In the 7th aspect, it provides a method for detecting the presence of RL9 and/or RL10 protein in a sample comprising: contacting the sample with an antibody specifically against RL9 and/or RL10 protein, and observing the formation of antibody complex which indicates the presence of RL9 and/or RL10 protein in the sample. It also provides a method for detecting tumor, comprising the step of detecting the presence of RL9 and/or RL10 in the sample of the subject, such as blood, urine, body fluid, and saliva.

In the 8th aspect, it provides a kit for detecting tumor comprising a pair of primers specifically amplifying RL9 and/or RL10 and/or an antibody specifically against RL9 and/or RL10 protein. The kit may further contain the specific probes and/or PCR buffers and so on.

In the 9th aspect, it provides the uses of RL9 and/or RL10 and their encoding sequence, e.g., in screening RL9 and/or RL10 agonists and antagonists, and in peptide fingerprinting. The RL9 and/or RL10 encoding sequence and the fragments thereof can be used as primers in PCR, or probes in hybridization and microarray.

In the 10th aspect, it provides a pharmaceutical composition comprising a safe and efficient amount of RL9 and/or RL10 antagonist and a pharmaceutically acceptable carrier. The preferred RL9 and/or RL10 antagonists are antibodies against RL9 and/or RL10 protein or antisense nucleotide sequence of RL9 and/or RL10 gene. The pharmaceutical composition can be used to treat tumors.

The other aspects of invention will be apparent to artisan in light of the teaching of the invention.

DESCRIPTION OF DRAWINGS

FIGS. 2A and 2B show chromosome BLAST results of RL4, RL9 and RL10 and the analysis of exons, respectively.

FIG. 3 shows the alignment of amino acid sequence of RL4 (SEQ ID NO: 10), amino acid sequence of RL9 (SEQ ID NO: 2) and amino acid sequence of RL10 (SEQ ID NO: 4).

FIG. 4 shows the alignment of nucleotide sequence of RL4 (SEQ ID NO: 9), nucleotide sequence of RL9 (Nucleotides 1-768 of SEQ ID NO: 1), and nucleotide sequence of RL10 (Nucleotides 1-639 of SEQ ID NO: 3).

DETAILED DESCRIPTION

Figure 1:
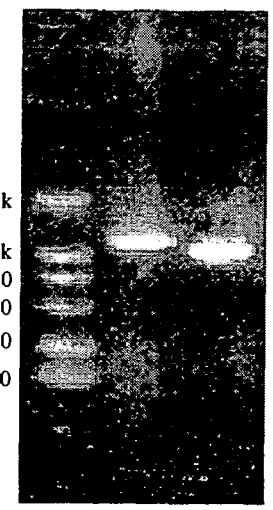
FIG. 1 shows the electrophoresis of RL9 and RL10 genes.

As used herein, the term "RL9/RL10" means "RL9 and/or RL10.

As used herein, the term "RL9 protein", "RL9 polypeptide" or "tumor tag RL9" are exchangeable, referring to a protein or polypeptide comprising or consisting of the amino acid sequence of tumor tag RL9 (SEQ ID NO: 2). The term also includes the mature RL9 without the signal peptide, i.e., 1-29 of SEQ ID NO: 2.

As used herein, the term "RL10 protein", "RL10 polypeptide" or "tumor tag RL10" are exchangeable, referring to a protein or polypeptide comprising or consisting of the amino acid sequence of tumor tag RL10 (SEQ ID NO: 4). The term also includes the mature RL10 without the signal peptide, i.e., 1-29 of SEQ ID NO: 4.

As used herein, the term "isolated" refers to a substance which has been isolated from the original environment. For naturally occurring substance, the original environment is the natural environment. E.g., the polynucleotide and polypeptide in a naturally occurring state in the viable cells are not isolated or purified. However, if the same polynucleotide and polypeptide have been isolated from other components naturally accompanying them, they are isolated or purified.

As used herein, the terms "isolated RL9/RL10 protein or polypeptide" mean that RL9/RL10 polypeptide does not essentially contain other proteins, lipids, carbohydrate or any other substances associated therewith in nature. The artisans can purify RL9/RL10 protein by standard protein purification techniques. Essentially purified polypeptide forms a single main band on a non-reductive PAGE gel.

The polypeptide of invention may be a recombinant polypeptide, natural polypeptide, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the protocol of recombinant production, the polypeptide of invention may be glycosylated or non-glycosylated. The polypeptide of invention may or may not comprise the starting Met residue.

The invention further comprises the fragments, derivatives and analogues of RL9/RL10. As used in the invention, the terms "fragment", "derivative" and "analogue" mean the polypeptide that essentially retains the same biological functions or activity of RL9/RL10 protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence, e.g., a fusion protein formed with IgC fragment. Such fragments, derivatives and analogs are deemed to be within the scope of those skilled in the art from the teachings herein.

In the present invention, the term "human RL9/RL10 polypeptide" refers to a full-length polypeptide having the activity of human RL9/RL10 protein comprising the amino acid sequence of SEQ ID NOs: 2 or 4, or the mature polypeptide thereof. The term also comprises the variants of said amino acid sequence which have the same function of human RL9/RL10. These variants include, but are not limited to, deletions, insertions and/or substitutions of several amino acids (typically 1-50, preferably 1-30, more preferably 1-20, most preferably 1-10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of RL9/RL10 protein.

The variants of polypeptide include homologous sequences, allelic variants, natural mutants, induced mutants, proteins encoded by DNA which hybridizes to RL9/RL10 DNA under high or low stringency conditions as well as the polypeptides or proteins retrieved by antisera raised against RL9/RL10 polypeptide. The present invention also provides other polypeptides, e.g., fusion proteins, which include the RL9/RL10 polypeptide or fragments thereof. In addition to substantially full-length polypeptide, the soluble fragments of RL9/RL10 polypeptide are also included. Generally, these fragments comprise at least 10, typically at least 30, preferably at least 50, more preferably at least 80, most preferably at least 100 consecutive amino acids of RL9/RL10 polypeptide.

The present invention also provides the analogues of RL9/RL10 protein or polypeptide. Analogues can differ from naturally occurring RL9/RL10 polypeptide by amino acid sequence differences or by modifications that do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

In the invention, "RL9/RL10 conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NOs: 2 or 4. Preferably, these conservative mutants are formed by the substitution according to Table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide according to the invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NOs: 1 or 3, or may be a degenerate sequence. As used herein, the term "degenerate sequence" means an sequence which encodes a protein or peptide comprising a sequence of SEQ ID NOs: 2 or 4 and which has a nucleotide sequence different from the sequence of coding region in SEQ ID NOs: 1 or 3.

The sequences encoding the mature RL9/RL10 polypeptide include those encoding only the mature polypeptide, those encoding mature polypeptide plus various additional encoding sequence, the encoding sequence for mature polypeptide plus the non-encoding sequence and optional additional encoding sequence. The term "polynucleotide encoding the polypeptide" includes the polynucleotide encoding said polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50%, preferably at least 70%, more preferably at least 80%, and most preferably at least 90% or 95% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 90%, preferably 95% homology. Further, the polynucleotides which hybridize to the hereinabove described polynucleotides encode a polypeptide which retains the same biological function or activity as the mature polypeptide shown in SEQ ID NOs: 2 or 4.

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding RL9/RL10 protein.

The full-length RL9/RL10 nucleotide sequence or its fragment can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized, especially when the fragment is short. Typically, several small fragments are synthesized and linked together to obtain a long sequence.

It is completely feasible to chemically synthesize the DNA sequence encoding the protein of invention, or the fragments or derivatives thereof. Then, the DNA sequence can be introduced into the various DNA molecules (such as vectors) and cells available in the art. In addition, the mutation can be introduced into the protein sequence by chemical synthesis.

The method of amplification of DNA/RNA by PCR is preferably used to obtain the gene of the invention. The primers used in PCR can be properly selected according to the polynucleotide sequence information of invention disclosed herein and synthesized by the conventional methods. The amplified DNA/RNA fragments can be isolated and purified by conventional methods such as gel electrophoresis.

The invention further relates to a vector comprising the polynucleotide of the invention, a genetic engineered host cell transformed with the vector of the invention or directly with the sequence encoding RL9/RL10 protein, and the method for producing the polypeptide of invention by recombinant techniques.

The recombinant human RL9/RL10 polypeptides can be expressed or produced by the conventional recombinant DNA technology, using the polynucleotide sequence of invention. Generally, it comprises the following steps:

(1) transfecting or transforming the appropriate host cells with the polynucleotide or its variants encoding RL9/RL10 polypeptide of the invention or the vector containing said polynucleotide;

(2) culturing the host cells in an appropriate medium;

(3) isolating or purifying the protein from the medium or cells.

In the present invention, the polynucleotide sequences encoding human tumor tag may be inserted into a recombinant expression vector. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of RL9/RL10 and appropriate transcription/translation regulatory components. These methods include in vitro recombinant DNA technique, DNA synthesis technique, in vivo recombinant technique and so on. The DNA sequence is efficiently linked to the proper promoter in an expression vector to direct the synthesis of mRNA. The expression vector may further comprise a ribosome-binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.\ coli$.

The vector containing said DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as $E.\ coli, Streptomyces, Salmonella\ typhimurium$; fungal cells, such as yeast; plant cells; insect cells such as Drosophila S2 or Sf9; animal cells such as CHO, COS or 293 cells, etc.

Recombinant transformation of host cell with the DNA sequence of invention might be carried out by conventional techniques well known to those skilled in the art. Where the host is prokaryotic such as $E.\ coli$, the competent cells, which are capable of DNA uptake, can be prepared from cells harvested after exponential growth phase and subsequently treated by the $CaCl_2$ method using procedures well known in the art. Alternatively, $MgCl_2$ can be used. The transformation can also be carried out by electroporation, if desired. When the host is an eukaryote, such methods of transfection of DNA as calcium phosphate co-precipitates, conventional mechanical procedures such as micro-injection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

Therefore, the recombinant human RL9/RL10 protein or polypeptide have various uses including, but not to be limited to: screening out antibodies, polypeptides or other substances which inhibit the function of RL9/RL10 protein.

In another aspect, the invention also includes polyclonal and monoclonal antibodies (mAbs), preferably mAbs, which are specific for polypeptides encoded by RL9/RL10 DNA or fragments thereof. By "specificity", it means an antibody which binds to the RL9/RL10 gene products or a fragments thereof. Preferably, the antibody binds to the RL9/RL10 gene products or fragments thereof and does not substantially recognize nor bind to other antigenically unrelated molecules. Antibodies which bind to RL9/RL10 and block RL9/RL10 protein and those which do not affect the RL9/RL10 function are included in the invention.

The invention includes intact monoclonal or polyclonal antibodies, and immunologically-active antibody fragments, e.g., a Fab' or $(Fab)_2$ fragment, an antibody heavy chain, an antibody light chain, or a chimeric antibody.

The antibody against RL9/RL10 can be used in immunohistochemical method to detect the presence of RL9/RL10 protein in biopsy specimen.

The antibodies of the invention can be used to treat or prevent RL9/RL10-related human diseases such as tumor. One common method is to challenge the amino group on the antibody with sulfydryl cross-linking agents, such as SPDP, and bind the toxin onto the antibody by interchanging the disulfide bonds. This hybrid antibody can be used to kill RL9/RL10 protein-positive cells such as tumor cells.

The substances that act with RL9/RL10 protein, e.g., receptors, inhibitors, agonists and antagonists, can be screened out by various conventional techniques, using RL9/RL10 protein of the invention.

The RL9/RL10 protein, antibody, inhibitor, agonist or antagonist of the invention provide different effects when administrated in therapy. Usually, these substances are formulated with a non-toxic, inert and pharmaceutically acceptable aqueous carrier. The pH typically is about 5-8, preferably 6-8, although pH may alter according to the property of the formulated substances and the diseases to be treated. The formulated pharmaceutical composition is administrated in conventional routes including, but not limited to, intramuscular, intraperitoneal, intravenous, subcutaneous, intradermal or topical administration.

The RL9/RL10 antagonists such as antibody and antisense sequence can be directly used for curing disorders, e.g., tumors, which include, but are not limited to: stomach cancer, colon cancer, breast cancer, lung cancer, liver cancer, prostate cancer and leukemia. The RL9/RL10 protein can be administrated in combination with other medicaments, e.g., TNF-α, TNF-β and so on.

The invention also provides a pharmaceutical composition comprising safe and effective amount of RL9/RL10 antagonist in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections that are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 ug-10 mg/kg body weight per day.

The invention further provides diagnostic assays for quantitative and in situ measurement of RL9/RL10 protein level.

These assays are known in the art and include FISH assay and radioimmunoassay. The level of RL9/RL10 protein detected in the assay can be used to detect tumor.

A method of detecting RL9/RL10 protein in a sample by utilizing the antibody specifically against RL9/RL10 protein comprises the steps of: contacting the sample with the antibody specifically against RL9/RL10 protein; observing the formation of antibody complex which indicates the presence of RL9/RL10 protein in the sample.

The polynucleotide encoding RL9/RL10 protein can be used in the diagnosis and treatment of RL9/RL10 related diseases. A part of or all of the polynucleotides of the invention can be used as probe and fixed on a microarray or DNA chip for analyzing the differential expression of genes in tissues and for the diagnosis of genes. The RL9/RL10 specific primers can be used in RT-PCR and in vitro amplification to detect the transcripts of RL9/RL 10.

The invention also provides a kit for detecting tumor comprising a pair of primers specifically amplifying RL9/RL10 and/or an antibody specifically against RL9/RL10 protein. The kit may further contain the specific probes and/or PCR buffers and so on.

The sequencing data of RL9/RL10 showed that, RL9/RL10 shared high identity with another tumor tag of ULBP-4 disclosed in PCT/CN02/00137 filed by the present inventors. They bind to NKG2D and are mapped on the same position of the chromosome, indicating they are the different splicing forms of the same DNA fragment. The analysis of expression showed that, RL9/RL10 gene was expressed only in tumor tissues, while it was not expressed or low expressed in normal cells.

Further, it is of interest that RL9 can be secreted into the body fluid after it is cleaved by proteinase and RL10 is a secretory protein itself. Therefore, RL9 and RL10 are both effective tumor tags useful in the diagnosis and treatment of various cancers.

Since RL9 and RL10 are possibly tumor specific rejection antigens which are secreted into body fluid, the direct detection of RL9/RL10 in blood sample or urine sample can be used not only as an indication for auxiliary diagnosis and prognosis of tumor, but also as a basis for early diagnosis of tumor.

In addition to diagnosis application, RL9 and RL10 also has potential use in the tumor surgery. It is helpful to determine the depth and boundary of the tumor invasion and the hidden parts of tumor. In radioimmunoguided surgery (RIGS), a radioisotope labeled antibody against tumor-related antigen is injected into the body for imaging. Base on the analysis of images, the range of tumor invasion can be accurately determined.

In the respect of immunotherapy of tumor, RL9/RL10 or fusion protein containing RL9/RL10 can be used as immunostimulant, which binds to the NKG2D receptor on the surface of NK cells, γδ-TCR+ T cells, CD8+αβ-TCR+ T cells to activate these cells so that the cytotoxins are released to kill the tumor cells. Meanwhile, the cells against tumor are amplified in the body.

Since RL9 is on the cell surface, it is useful in the biologically targeting system. For example, a toxin-labeled monoclonal antibody against RL9 or soluble NKG2D can specifically bind to RL9 on the surface of tumor cells in vivo and kill tumor cells. In the tumor therapy, when these drugs are concentrated in the tumor region, the cure efficiency can be increased while the damage to the whole body can be lowered.

In the respect of tumor vaccine, RL9/RL10 is useful in preparing molecular tumor vaccine. Tumor vaccine is the main portion of active immunity and is classified into 4 types, i.e., cell tumor vaccine, sub-cell tumor vaccine, molecular tumor vaccine and gene tumor vaccine. The former two types are previous tumor vaccines having very different clinical effects, most of which are not ideal for long-term therapy. The molecular tumor vaccine is based on the interaction between antibody and antigen so that an idiotype antibody against tumor can be prepared. As an idiotype tumor vaccine, it has certain clinical effects. The tumor antigenic peptide can be produced industrially without the risk associated with tumor inoculation and without inhibitory components from tumor cells. When RL9/RL10 is used as a tumor antigenic peptide, the resultant molecular vaccine is not limited by the MHC and is applicable to various tumors. In addition to molecular tumor vaccine, another preferred type of tumor vaccine is gene tumor vaccine formed by inserting RL9/RL10 gene in series into the viral vector.

Moreover, the extramembral portion of RL9 is useful to enhance immunity. It can bind to NKG2D, thereby activating immunity cells such as NK cells and T cells so as to enhance immunity.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Isolation of RL9, RL10 Genes

By bio-informatics analysis, the inventor predicted, at the RL4 gene locus, there were new gene isoforms, formed by different splicing of the same DNA sequence. Several pairs of primers were synthesized for the cloning of RL9 and RL10 genes out of a cDNA library. Standard PCR was performed using a human Jurkat cell cDNA library and HELA cell cDNA library conventionally constructed as the template and the following designed primers (same primers were used for RL9 and RL10).

```
Forward:
                                        (SEQ ID NO: 5)
5'-ATGCGAAGAATATCCCTGACTTCTAG-3'

Reverse:
                                        (SEQ ID NO: 6)
5'-CCTCACTTTTCTTCTCTCCCTCTCACACATAG-3'
```

As shown in FIG. 1, one band was obtained by PCR using this pair of primers from Jurkat cell cDNA and one from HELA cell cDNA library. Both bands were approximately 1000 bp in size, by 200 bp difference in size. These two fragments were isolated, cloned into a vector and sequenced. A 1267 bp sequence (RL9) and a 1043 bp sequence (RL10) were obtained. After analysis, it was found that these two DNA fragments were highly homologous, but they were two novel genes with two complete coding regions.

EXAMPLE 2

Sequence Analysis and Mapping of RL9 and RL10 Gene

Two DNA fragments obtained in Example 1 included two whole coding regions, and therefore, they were named as RL9 and RL10. The sequence information were as follows:

| Gene name | Nucleotide sequence | Coding region | Protein length |
|---|---|---|---|
| RL9 | 1267 bp (SEQ ID NO: 1) | 1-768 | 255AA (SEQ ID NO: 2) |
| RL10 | 1043 bp (SEQ ID NO: 3) | 1-639 | 212AA (SEQ ID NO: 4) |

RL9 and RL10 were mapped onto the same locus on Chromosome 6 as RL4 (SEQ ID NO:9 and 10): 6q25.1.

The results of homology comparison on nucleotide level between the coding region of RL9, RL10 and other family members of RL (RL1-5) were as follows:

| | Seq-> | | | | | | |
|---|---|---|---|---|---|---|---|
| | RL1 | RL2 | RL3 | RL4 | RL5 | RL9 | RL10 |
| RL1 | 1.000 | 0.715 | 0.334 | 0.385 | 0.678 | 0.367 | 0.378 |
| RL2 | — | 1.000 | 0.311 | 0.387 | 0.811 | 0.399 | 0.375 |
| RL3 | — | — | 1.000 | 0.261 | 0.284 | 0.269 | 0.235 |
| RL4 | — | — | — | 1.000 | 0.339 | 0.952 | 0.785 |
| RL5 | — | — | — | — | 1.000 | 0.350 | 0.419 |
| RL9 | — | — | — | — | — | 1.000 | 0.809 |
| RL10 | — | — | — | — | — | — | 1.000 |

Figure 2A:
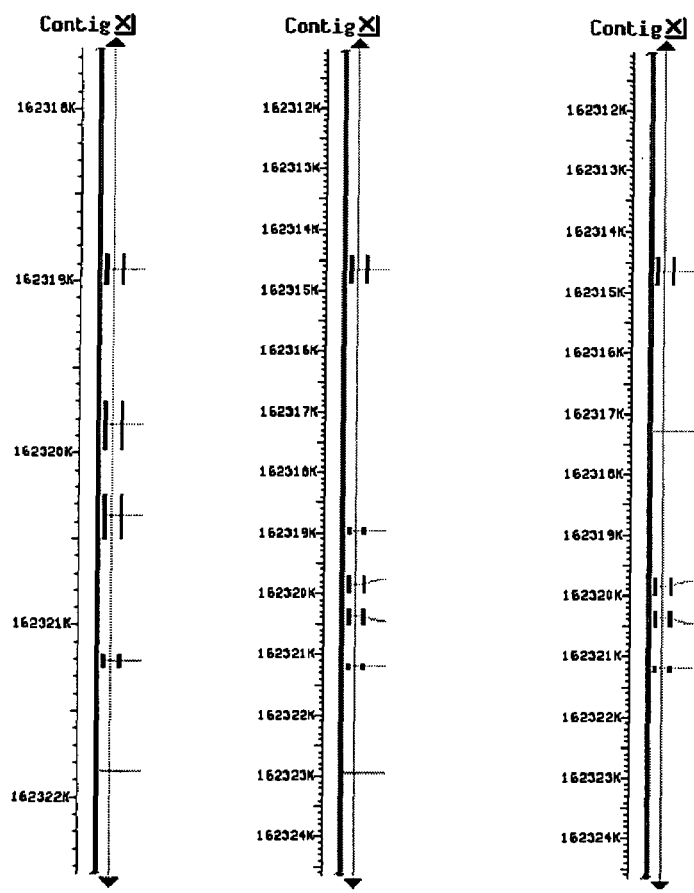

The results showed that RL4 shared the highest homology with RL9 and RL10, consistent with the prediction that RL4, RL9 and RL10 were different splicing isoforms from the same DNA sequence. Chromosome BLAST and exon analysis also confirmed that RL4, RL9 and RL10 were formed by different splicing (FIGS. 2A and 2B).

Nucleotide sequence alignment and protein sequence alignment showed that the first 652 bp in RL4 and RL9 were identical, and first 623 bp in RL10 shared 99% homology with those in RL4 and RL10. RL4, RL9 and RL10 also shared high homology on protein level (FIGS. 3 and 4).

EXAMPLE 3

Study on Protein Sequence of RL9 and RL10

Software analysis of the protein structure of RL9 and RL10 by ExPASy (Expert Protein Analysis System) proteomics server provided by Swiss Institute of Bioinformatics (SIB) showed the following results: (Protein sequence analysis: Translate; Signal peptide analysis: SignalP; Transmembrane structure analysis: Tmpred; GPI structure analysis: DGPI)

| Protein name | Length (aa) | Signal peptide | GPI | Secreted or not |
|---|---|---|---|---|
| RL4 | 263 | 1-29AA | YES | NO |
| RL9 | 255 | 1-29AA | NO | NO |
| RL10 | 212 | 1-29AA | NO | YES |

Figure 5:
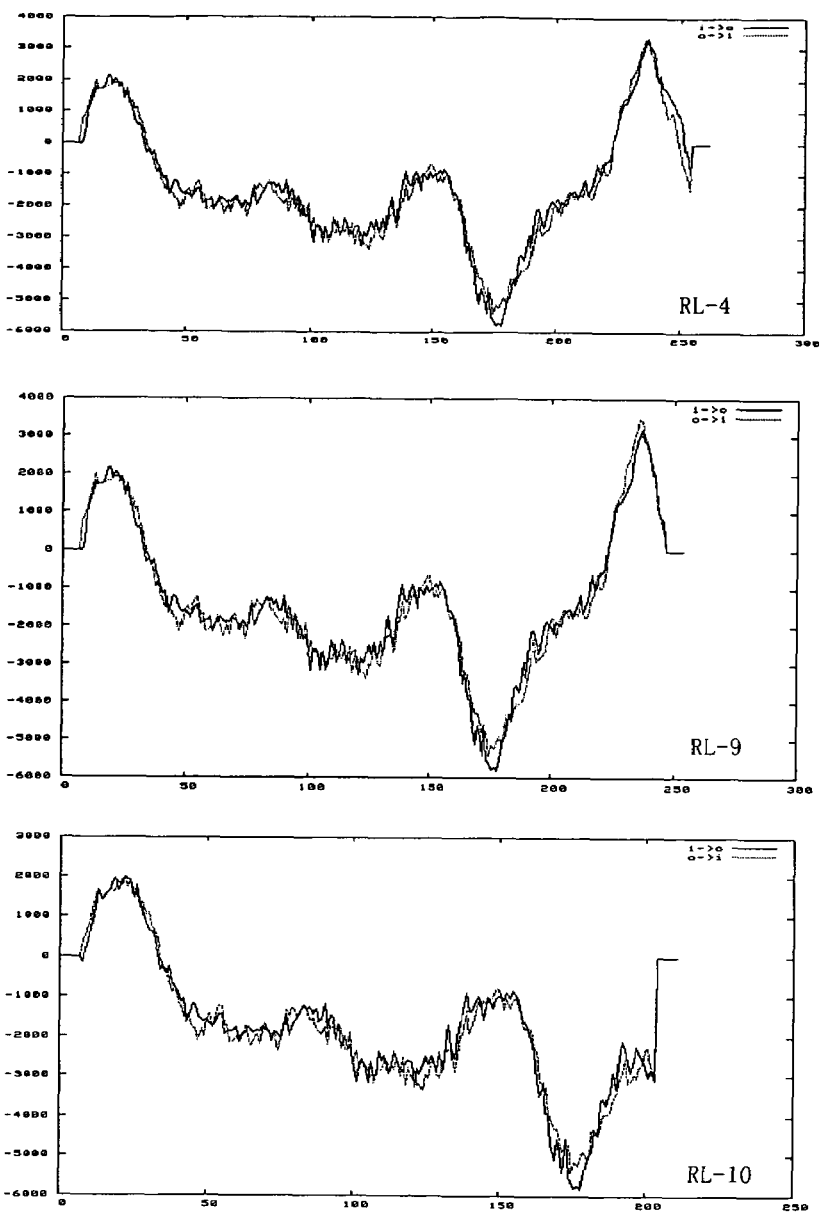
FIG. 5 shows the analysis of transmembrane regions of RL4, RL9 and RL10 proteins.

The result of transmembrane analysis was shown in FIG. 5. When compared with RL4, RL9 still had a transmembrane region although more than 10 amino acids were deleted in RL9. However, the whole transmembrane region was missing in RL10, indicating RL10 was a secretory protein.

EXAMPLE 4

Recombinant Expression and Purification of RL9 Protein

The extracellular sequence of RL9 and RL10 shared high similarity, only with three amino acids in difference. Therefore, one of them, i.e., RL9 was chosen for recombinant expression and purification.

In this example, the DNA sequence encoding human RL9 was amplified with the following oligonucleotide PCR primers corresponding to 5'- and 3'-end of RL9 DNA sequence using the PCR product obtained in Example 1 as the template. The resultant RL9 DNA was used as an insertion fragment.

The sequence of 5'-end oligonucleotide primer was:

```
                                           (SEQ ID NO: 11)
5'- ccgggatcc TTGGAGATCATGGTTGGTGGTCACT-3'
```

This primer contained a cleavage site of restriction endonuclease BamHI, followed by the coding sequence of RL9 without the signal peptide sequence.

The sequence of 3'-end primer was:

```
                                           (SEQ ID NO: 12)
5'- ggccaagcttCCATCTATCTGGTAGACTAGAAGAA-3'
```

This primer contained a cleavage site of restriction endonuclease HindIII, a stop codon and part of coding sequence of human RL9.

The PCR product of human RL9 cDNA was purified, digested with BamHI/HindIII and linked into plasmid pProEXHTa (GIBCO BRL) according to the conventional method, thereby forming vector pProEXHTa-RL9. The vector pProEXHTa-RL9 was transformed into competent E. coli DH5α. The positive clones were identified, selected and sequenced (Model 377 sequencing machine from ABI company; BigDye Terminator kit from PE company). The sequencing results confirmed that the whole coding sequence of RL9 was inserted into the vector successfully.

The positive DH5α clone expressing RL9 was inoculated in 10 ml LB liquid medium and cultured in 37° C. overnight at 300 rpm, then added to fresh LB medium at 1:100 dilution and cultured for another 2.5 hr. 100 mM IPTG was added to final concentration of 0.1 mM and the bacteria were cultured for another 2-3 hr. RL9 was purified using the following procedure: The bacteria after induction were harvested by centrifugation at 5000 g for 10 minutes at 4° C. The supernatant was removed and pellet was resuspended with 50 ml loading buffer (0.5M NaCl, 20 mM imidozole, 2.7 mM KCl, 10.1 mM $Na_2HPO_4$, 1.8 mM $KH_2PO_4$, pH 8.0) on ice. The bacteria were sonicated so as to break the cells (B. Braun Labsonic U). The lysate was centrifuged at 12,000 g for 10 minutes at 4° C. After filtrated with 0.8-micrometer membrane filter, the supernatant was flowed through 1 ml $Ni^{2+}$ metal chelating Sepharose 4B chromatography column. After sufficiently washing with loading buffer, the column was eluted with 500 ul imidozole elution buffer (0.5M NaCl, 500 mM imidozole, 2.7 mM KCl, 10.1 mM $Na_2HPO_4$, 1.8 mM $KH_2PO_4$, pH 8.0). After standing at room temperature for 30 minutes, eluate was collected. The elution procedure was repeated for 2-3 times and RL9 protein was obtained.

EXAMPLE 5

Preparation of Antibody Against RL9

Antibodies were produced by immunizing animals with the recombinant human RL9 proteins obtained in Example 4. The method was as follows: the recombinant proteins were isolated by chromatography, and stored for use. Alternatively, the protein was isolated by SDS-PAGE electrophoresis, and obtained by cutting electrophoretic bands from gel. The protein was emulsified with Freund's complete adjuvant of the same volume. The emulsified protein was injected intraperitoneally into mice at a dosage of 50-100 ug/0.2 ml. 14 days later, the same antigen was emulsified with Freund's incomplete adjuvant and injected intraperitoneally into mice at a dosage of 50-100 ug/0.2 ml for booster immunization. Booster immunization was carried out every 14 days, for at least three times. The specific activity of the obtained antiserum was evaluated by its ability of precipitating the translation product of RL9 gene in vitro. The results confirmed that the specific binding between the antibody and the RL9 protein of the invention.

EXAMPLE 6

Tissue Expression Spectrum and Quantitative PCR Analysis of RL9 and RL10

To further confirm the expression of RL9 in various tumor tissues, RT-PCR and real time fluorescent quantitative PCRs were used to study the qualitative and quantitative expression of RL9 in intestine tumor tissues.

7 pairs of intestine tumor tissues and their corresponding normal tissues were selected, wherein N represented normal tissues and T represented tumor tissues. The following internal primers in RL9 encoding region was used to determine the expression pattern of RL9 in the selected 7 pairs tissues:

```
5'-GACCTGGACAGTAATTAATC-3'    (SEQ ID NO: 7)

5'-TTGACTCAGGGAACACAC-3'      (SEQ ID NO: 8)
```

The RT-PCR results showed that, the expression of RL9 was increased in some tumor tissues compared to the corresponding normal tissues.

Conventional quantitative PCR was used to get more precise analysis of RL9 expression. The results were as follows:

RL9 and RL10 were useful as tumor markers because they were specifically expressed in tumor tissues and no expression was detected in most normal tissues. RL9 and RL10 could be used as indicators for tumor diagnosis.

EXAMPLE 7

RL9 was a Transmembrane Protein

To confirm RL9 was a transmembrane protein, RL9 cDNA was subcloned into a conventional eukaryotic expression vector pCDEF3-FLAG with a flag epitope at its carboxyl terminal, thereby forming pCDEF3-RL9-FLAG. 293T cells were transfected by pCDEF3-RL9-FLAG. Cells and supernatant of the cell culture were harvested after culturing for 24 hours. After cell lysis, anti-FLAG M2 antibody was used to immunoprecipitate the supernatant of cell culture. The anti-FLAG M2 antibody was used in the Western blotting for cell lysate, supernatant of cell culture, and the immunoprecipitates from the supernatant.

Figure 6:
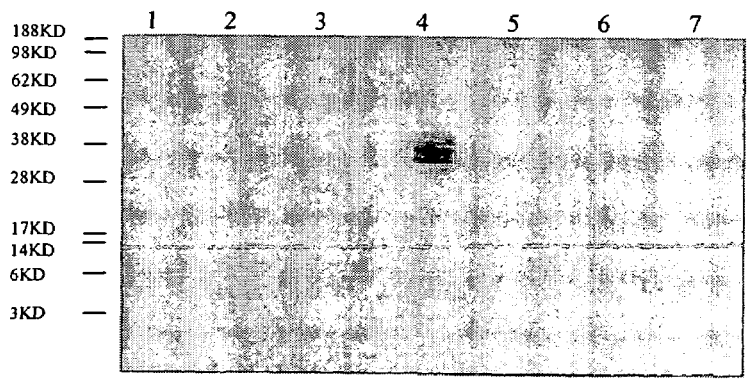
FIG. 6 shows the expression of RL9. Lane 1: the whole cell lysate of 293T; Lane 2: the supernatant of 293T; Lane 3: the immunoprecipitates of the supernatant of 293T; Lane 4: the whole cell lysate of 293T cell transfected with RL9; Lane 6: the supernatant of 293T cell transfected with RL9; Lane 7: immunoprecipitates of the supernatant of 293T cell transfected with RL9.

As shown in FIG. 6, most of the RL9-FLAG protein existed in the cell lysate of transfected 293T cells, indicating RL9 was a transmembrane protein indeed. The fusion protein of RL9-FLAG was about 38 kDa in size as shown in FIG. 6. After exclusion the molecular weight of FLAG, the molecular weight of RL9 was consistent with the prediction, i.e., about 25 kDa.

EXAMPLE 8

Interaction between RL9, RL10 and NKG2D

The mice Ba/F3 cell line was transfected with a retrovirus expression vector containing RL9 or RL10 cDNA conventionally constructed. The transfected Ba/F3 cells were labeled with soluble NKG2D-Ig fusion protein or human Ig as a control. After immuno-fluorescence labeling, the cells were analyzed by FACS.

FACS results showed that cells transfected with RL9 or RL10 gene interacted with NKG2D specifically, not only confirming the expression of RL9 and RL10 in mammalian cells, but also indicating the gene products of RL9 and RL10 were ligands of NKG2D.

| Tissue | Intestine tissue sample | Ratio of RL9 vs. actin in normal tissue (e-6) | Ratio of RL9 transcript vs. actin in tumor tissue (e-6) |
|---|---|---|---|
| rectum | 2N-2T | 0.00 | 44.70 |
| right semicolon | 3N-3T | 0.00 | 8.91 |
| ascending colon | 4N-4T | 0.00 | 2.24 |
| rectum | 5N-5T | 7.07 | 17.61 |
| sigmoid colon | 6N-6T | 0.00 | 6.78 |
| sigmoid colon | 7N-7T | 0.00 | 11.98 |
| colon | 8N-8T | 0.00 | 0.00 |

The results of quantitative PCR showed that RL9 was tumor-specific. The expression of RL9 in tumor tissue was increased compared to the corresponding normal tissues for most pairs.

Similar experiments were performed for RL10. The expression of RL10 in tumor tissue was increased compared to the corresponding normal tissues for most pairs.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. An isolated polynucleotide which encodes a polypeptide comprising the amino acid sequence selected from the group consisting of:

(a) the amino acid sequence of 1-255 of SEQ ID NO: 2; and (b) the amino acid sequence of 30-255 of SEQ ID NO: 2.

2. An isolated polynucleotide which is selected from the group consisting of:

(a) the nucleotide sequence of 1-768 of SEQ ID NO: 1;

(b) the nucleotide sequence of 1-1267 of SEQ ID NO: 1; and (e) the nucleotide sequence of 88-768 of SEQ ID NO: 1.

3. A method for producing a polypeptide, which comprises the steps of:
(a) culturing a genetically engineered host cell comprising a vector containing the polynucleotide of claim 2 under the expression conditions; and
(b) isolating the polypeptide from the culture, wherein the polynucleotide is selected front the group consisting of:
(a) the nucleotide sequence of 1-768 of SEQ ID NO: 1;
(b) the nucleotide sequence of 1-1267 of SEQ ID NO: 1; and
(e) the nucleotide sequence of 88-768 of SEQ ID NO: 1.

4. A vector containing the polynucleotide of claim 1.

5. An isolated genetically engineered host cell comprising the vector of claim 4.

* * * * *